United States Patent [19]

Aquila et al.

[11] 4,113,781

[45] Sep. 12, 1978

[54] PHENYLPROPANALS

[75] Inventors: Werner Aquila, Mannheim; Werner Hoffmann, Neuhofen; Walter Himmele, Walldorf; Hardo Siegel, Ludwigshafen, all of Fed. Rep. of Germany

[73] Assignee: BASF Aktiengesellschaft, Ludwigshafen am Rhein, Fed. Rep. of Germany

[21] Appl. No.: 494,457

[22] Filed: Aug. 5, 1974

[30] Foreign Application Priority Data

Aug. 11, 1973 [DE] Fed. Rep. of Germany ....... 2340812

[51] Int. Cl.² .............................................. C07C 47/52
[52] U.S. Cl. ................................ 260/599; 260/600 R; 252/522
[58] Field of Search ......................................... 260/599

[56] References Cited

U.S. PATENT DOCUMENTS

| 2,875,131 | 2/1959 | Carpenter et al. | 260/599 |
| 2,880,241 | 3/1959 | Hughes | 260/599 |
| 3,555,098 | 1/1971 | Olivier et al. | 260/599 |
| 3,801,646 | 4/1974 | Booth | 260/599 |

FOREIGN PATENT DOCUMENTS

| 1,141,499 | 3/1957 | France | 260/599 |

*Primary Examiner*—Bernard Helfin
*Attorney, Agent, or Firm*—Keil, Thompson & Shurtleff

[57] ABSTRACT

Substituted phenylpropanals and a process for their manufacture by reaction of the corresponding phenylethenes with carbon monoxide and hydrogen at temperatures of from 50° to 180° C and pressures of from 20 to 1,500 atmospheres gauge, in the presence of rhodium carbonyl complexes. The phenylpropanals according to the invention have pleasant scents. 3-(4-Isopropyl-phenyl)-butanal-1 and 3-(4-tert.-butyl-phenyl)-butanal-1, in particular, have suitable scents for the preparation of flower oil. They are also valuable starting materials for synthesizing drugs, plant protection agents and dyes.

1 Claim, No Drawings

PHENYLPROPANALS

The invention is concerned with phenylpropanals of the formula

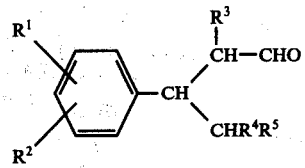

in which $R^1$ and $R^2$ are identical or different and each is hydrogen, halogen, alkyl of 1 to 7 carbon atoms, cycloalkyl of 3 to 8 carbon atoms or alkoxy of 1 to 4 carbon atoms, and $R^3$, $R^4$ and $R^5$ are identical or different and each is hydrogen or alkyl of 1 to 7 carbon atoms, with the proviso that at least one of the substituents $R^1$ to $R^5$ is not hydrogen.

We have found that phenylpropanals of the formula I

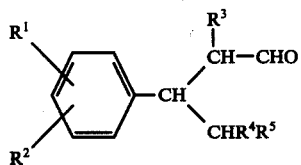

in which $R^1$ and $R^2$ are identical or different and each is hydrogen, halogen, alkyl of 1 to 7 carbon atoms, cycloalkyl of 3 to 8 carbon atoms or alkoxy of 1 to 4 carbon atoms, and $R^3$, $R^4$ and $R^5$ are identical or different and each is hydrogen or alkyl of 1 or 7 carbon atoms, with the proviso that at least one of the substituents $R^1$ to $R^5$ is not hydrogen, are obtained in an advantageous manner when compounds of the formula II

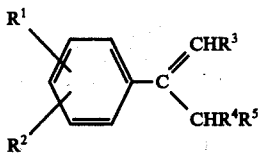

in which $R^1$ to $R^5$ have the above meanings, are reacted with carbon monoxide and hydrogen at temperatures of from 50° to 180° C. and under pressures of from 20 to 1,500 atmospheres gauge in the presence of rhodium carbonyl complexes.

It is an advantage of the new process that it makes a large number of new substituted phenylpropanals accessible. It is a further advantage of the new process that it gives good yields.

In those starting compounds of the formula II which are preferred because they are readily accessible, $R^1$ and $R^2$ can be identical or different and each is hydrogen or alkyl or alkoxy of 1 to 4 carbon atoms, fluorine, chlorine or bromine or cycloalkyl of 5 to 8 carbon atoms in the ring and $R^3$, $R^4$ and $R^5$ can be identical or different and each is hydrogen or alkyl of 1 to 4 carbon atoms, and the proviso that at least one of the substituents $R^1$ to $R^5$ is not hydrogen still applies. Examples of suitable starting compounds of the formula II are: 3-phenyl-pentene-2, 4-phenyl-heptene-3, 5-phenyl-nonene-4, 6-phenyl-undecene-5, 2-(4-methylphenyl)-propene-1, 3-(4-methyl-phenyl)-pentene-2, 5-)4-methyl-phenyl)-nonene-4, 2-(3-methyl-phenyl)-propene-1, 2-(2-methyl-phenyl)-propene-1, 2-(4-isopropyl-phenyl)-propene-1, 2-(4-tert.-butyl-phenyl)-propene-1, 2-(4-n-butyl-phenyl)-propene-1, 2-(4-sec.butyl-phenyl)-propene-1, 2-(4-tert.a-myl-phenyl)-propene- 1, 2-(4-ethyl-phenyl)-propene-1, 2-(4-n-propyl-phenyl)-propene-1, 3-(4-isopropyl-phenyl)-pentene-2, 2-(2-methoxy-phenyl)-propene-1, 2-(4-methoxy-phenyl)-propene-1, 2-(2,4-dimethoxy-phenyl)-propene-1, 2-(3,4-dimethoxy-phenyl)-propene-1, 2-(4-ethoxy-phenyl)-propene-1, 2-(4-propoxy-phenyl)-propene-1, 2-(4-isopropoxy-phenyl)-propene-1, 2-(4-fluorophenyl)-propene-1, 2-(3-fluorophenyl)-propene-1, 2-(2-fluorophenyl)-propene-1, 2-(4-chlorophenyl)-propene-1, 2-(4-chlorophenyl)-propene-1, 2-(2,6-dichlorophenyl)-propene-1, 2-(4-cyclohexyl-phenyl)-propene-1, 2-(4-cyclopropyl-phenyl)-propene-1, 2-(4-cyclopentylphenyl)-propene-1, 2-(3,4-dimethyl-phenyl)-propene-1, 2-(2,6-dimethyl-phenyl)-propene-1, 2-(2,4,6-trimethyl-phenyl)-propene-1, 2-(2,3,5-trimethyl-phenyl)-propene-1, 2-(2-trifluoromethyl-phenyl)-propene-1, 2-(4-trifluoromethyl-phenyl)-propene-1, 3-(2-methyl-phenyl)-pentene-2, 3-(3-methyl-phenyl)-pentene-2, 3-(4-ethyl-phenyl)-pentene-2, 3-(4butyl-phenyl)-pentene-2, 3-(4-tert.-butyl phenyl)-pentene-2, 3-(3,4-dimethyl-phenyl)-pentene-2, 3-(2,6-dimethyl-phenyl)-pentene-2, 3-(2,4,6-trimethyl-phenyl)-pentene-2, 3-(2,3,5-trimethyl-phenyl)-pentene-2, 3-(2-trifluoromethyl-phenyl)-pentene-2, 3-(3-trifluoromethyl-phenyl)-pentene-2, 3-(4-trifluoromethyl-phenyl)-pentene-2, 3-(2-methoxy-phenyl)-pentene-2, 3-(4-methoxy-phenyl)-pentene-2, 3-(2,4-dimethoxy-phenyl)-pentene-2, 3-(3,4-dimethoxy-phenyl)-pentene-2, 3-(2-fluorophenyl)-pentene-2, 3-(3-fluorophenyl)-pentene-2, 3-(4-fluorophenyl)-pentene-2, 3-(4-chlorophenyl)-pentene-2, 3-(2,6-dichlorophenyl)-pentene-2, 3-(4-cyclohexyl-phenyl)-pentene-2, 3-(4-cyclopentyl-phenyl)-pentene-2, 4-(4methyl-phenyl)-heptene-3, 4-(2-methyl-phenyl)-heptene-3, 4-(4-ethyl-phenyl)-heptene-3, 4-(4-isopropyl-phenyl)-heptene-3, 4-(4-tert.-butyl-phenyl)-heptene-3, 4-(3,4-dimethyl-phenyl)-heptene-3, 4-(2-methoxy-phenyl)-heptene-3, 4-(4-methoxy-phenyl)-heptene-3, 4-(4-propoxy-phenyl)-heptene-3, 4-(2,4-dimethoxy-phenyl)-heptene-3, 4-(3,4-dimethoxy-phenyl)-heptene-3, 4-(2-fluorophenyl)-heptene-3, 4-(3-fluorophenyl)-heptene-3, 4-(4-fluorophenyl)-heptene-3, 4-(4-chlorophenyl)-heptene-3, 4-(2,6-dichlorophenyl)-heptene-3, 4-(4-cyclohexyl-phenyl)-heptene-3, 4-(4-cyclopentyl-phenyl)-heptene-3, 5-(4-tert.-butyl-phenyl)-nonene-4, 5-(4-methoxy-phenyl)-nonene-4, 5-(4-fluorophenyl)-nonene-4, 5-(4-chlorophenyl)-nonene-4, 5-(2,4-dimethoxy-phenyl)-nonene-4, 5-(3-trifluoromethyl-phenyl)-nonene-4, 5-(2,6-dichlorophenyl)-nonene-4, 6-(4-methyl-phenyl)-undecene-5 and 6-(4-methoxy-phenyl)-undecene-5.

Of course, the preferred starting compounds give the preferred compounds of the formula I.

The process according to the invention is of very particular importance for the manufacture of phenylpropanals of the formula I

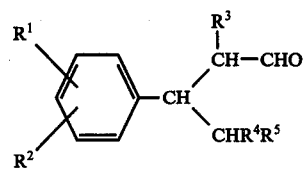

in which $R^1$ is alkyl of 1 to 4 carbon atoms, in the p-position, and $R^2$ to $R^5$ are hydrogen, by reaction of the corresponding compounds of the formula II with carbon monoxide and hydrogen in the presence of rhodium carbonyl complexes, since these phenylpropanals, especially 3-(4-isopropyl-phenyl)-butanal-1 and 3-(4-tert.-butyl-phenyl)-butanal-1, have outstanding scents.

Carbon monoxide and hydrogen are in general employed in a volume ratio of from 4:1 to 1:4, and in particular in a volume ratio of from 2:1 to 2:1. It is possible to use stoichiometric amounts, based on the starting material used, of the said gas mixture, but preferably an excess of the carbon monoxide and hydrogen is used, for example up to a 100-fold molar amount.

The reaction is carried out at temperatures of from 50° to 180° C.; temperatures of from 60° to 130° C. have proved particularly suitable. Further, pressures of from 20 to 1,500 atmospheres gauge are used for the reaction. Particularly good results are obtained under pressures of from 100 to 700 atmospheres guage.

The reaction is carried out in the presence of rhodium carbonyl complexes. In general, from 0.001 ppm to 0.05% by weight of rhodium, calculated as metal and based on the amount of the compounds of the formula II employ, is used. From 0.1 to 100 ppm of rhodium has proved to be a particularly advantageous amount. The carbonyl complexes of rhodium can be prepared separately before the reaction, or the corresponding starting materials, namely the halides, oxides, chelates or fatty acid salts of rhodium, can be fed separately to the reaction. The catalyst then forms in situ under the reaction conditions. Particularly advantageous starting materials are square-planar rhodium-(I) complexes, which give a homogeneous solution in the reaction mixture, such as dimeric fhodium carbonyl chloride, dimeric cyclooctadien-1,5-yl-rhodium chloride or rhodium carbonyl acetylacetonate.

Particularly advantageous results are obtained when tertiary organic phosphines are additionally used as catalyst modifiers. Tertiary phosphines wherein the substituents are alkyl radicals of 1 to 16 carbons atoms, cycloalkyl radicals of 5 to 8 carbon atoms or phenyl radicals which can optionally be substituted by alkyl radicals of 1 to 4 carbon atoms have proved particularly valuable. Triaryl phophines derived from benzene, for example triphenylphosphine, tritolylphosphine and mixed substituted phosphines, such as methyldiphenylphosphine, are especially suitable. The phosphines used as modifiers are employed in amounts of from 0.25 to 30 moles per gram atom of rhodium.

It is possible to carry out the reaction without solvents. In that case, the olefinically unsaturated compounds used as starting materials, and their hydroformylation products, serve as solvents. However, it is advantageous to use, in the reaction solvents which are inert and liquid under the reaction conditions, such as hydrocarbons, for example benzene, toluene, cyclohexane, hexane or octane, ethers, such as tetrahydrofuran or dioxane, or alkanols, such as methanol or butanol.

By way of example, the process according to the invention can be carried out by first introducing the starting compounds of the formula II, optionally together with one of the inert solvents described, and the stated amounts of catalysts, into a high pressure vessel and reacting with a mixture of carbon monoxide and hydrogen, of the stated composition, at the stated pressures and temperatures. After cooling, and releasing the pressure, the reaction mixture is separated from the catalysts by distillation. The end products of the formula I can be isolated without difficulty from the mixture thus obtained, by conventional methods; for example fractional distillation. Unconverted starting materials can be recycled to the reaction. The process according to the invention can also easily carried out continuously in suitable equipment.

The compounds of the formula I possess pleasant scents, and 3-(4-isopropyl-phenyl)-butanal-1 and 3-(4-tert.-butyl-phenyl)-butanal-1 in particular have a suitable type of odor for the preparation of flower oil such as lavender, lily of the valley, linden, iris, lily, lilac or cyclamen. The compounds according to the invention are also valuable starting materials for the synthesis of pharmacologically active materials, plant protection agents and dyes.

The Examples which follow illustrate the manufacture of the compounds of the formula I. The abbreviation COD represents cyclooctadienyl-1,5.

EXAMPLE 1

3,000 g of 2-(4-isopropyl-phenyl)-propene-1 and 75 mg of dimeric cyclooctadien-1,5-yl-rhodium chloride $(Rh(Cl)COD)_2$ in 3,000 ml of benzene as the solvent are heated to 110° C. in a high pressure autoclave of 10 l capacity and reacted with a mixture of carbon monoxide and hydrogen (volume ratio 55:45) under a pressure of 600 atmospheres gauge. The pressure is maintained for 10 hours by injection of further gas mixture. After completion of the reaction, the autoclave is cooled under pressure, and the pressure is then released. The reaction mixture is fractionally distilled in a column, the main fraction passing over at 103° C./1.0 mm Hg. In total, 2,918 g of 3-(4-isopropyl-phenyl)-butanal-1 are obtained. The 2,4-dinitrophenylhydrazone of the aldehyde melts at from 108° to 109° C.

EXAMPLE 2

150 g of 3-phenylpentene-2 and 50 ppm of rhodium as $(Rh(Cl)COD)_2$, in 200 ml of benzene as the solvent, are heated to 110° C. in a high pressure vessel of 0.81 capacity and reacted with carbon monoxide any hydrogen (volume ratio $CO:H_2 = 1:1$) under a pressure of 600 atmospheres gauge. The pressure is maintained constant by injection of further gas mixture. Gas corresponding to a pressure drop of 220 atmospheres gauge is consumed in the course of 4 hours. The autoclave is then cooled under pressure, the pressure is released and the mixture is worked up by distillation. 143 g of 2-methyl-3-phenyl-pentanal-1 of boiling point 121 to 123° C./14 mm Hg are obtained.

EXAMPLE 3 TO 12

The precedure described in Example 1 or 2 is followed. Using the starting materials listed in the table which follows, the phenylpropanals shown in the table are obtained.

| Example | Olefin | Aldehyde | Boiling point | Melting point, DNPH[1] |
|---|---|---|---|---|
| 3 | H₃C–C₆H₄–C(CH₃)=CH₂ | H₃C–C₆H₄–CH(CH₃)–CH₂–CHO | 66 to 68° C/ 0.2 mm Hg | 104 to 105° C |
| 4 | 3,4-(H₃C)₂–C₆H₃–C(CH₃)=CH₂ | 3,4-(H₃C)₂–C₆H₃–CH(CH₃)–CH₂–CHO | 146° C/18 mm Hg | 135 to 136° C |
| 5 | (H₃C)₃C–C₆H₄–C(CH₃)=CH₂ | (H₃C)₃C–C₆H₄–CH(CH₃)–CH₂–CHO | 100° C/0.5 mm Hg | 116 to 117° C |
| 6 | o-CH₃O–C₆H₄–C(CH₃)=CH₂ | o-CH₃O–C₆H₄–CH(CH₃)–CH₂–CHO | 113° C/2.00 mm Hg | 112° C |
| 7 | F–C₆H₄–C(CH₃)=CH₂ | F–C₆H₄–CH(CH₃)–CH₂–CHO | 100° C/0.4 mm Hg | 125° C |
| 8 | C₆H₁₁–C₆H₄–C(CH₃)=CH₂ | C₆H₁₁–C₆H₄–CH(CH₃)–CH₂–CHO | 108° C/0.1 mm Hg | 136° C |
| 9 | H₃CO–C₆H₄–C(=CH–CH₃)(CH₂–CH₃) | H₃CO–C₆H₄–CH–C(CHO)(CH₃)(CH₂–CH₃) | 135° C/2 mm Hg | 145 to 147° C |
| 10 | 3,4-(H₃C)₂–C₆H₃–C(=CH₂–CH₂–CH₃)(CH₂–CH₂–CH₃) | 3,4-(H₃C)₂–C₆H₃–CH–C(CHO)(CH₂–CH₃)(CH₂–CH₂–CH₃) | 129° C/0.2 mm Hg | 126 to 128° C |
| 11 | H₃CO–C₆H₄–C(=CH–CH₂–CH₃)(CH₂–CH₂–CH₃) | H₃CO–C₆H₄–CH–CH(CHO)(CH₂–CH₃)(CH₂–CH₂–CH₃) | 133° C/0.3 mm Hg | 161° C |
| 12 | C₆H₅–C(=CH–CH₂–CH₃)(CH₂–CH₂–CH₃) | C₆H₅–CH–CH(CHO)(CH₂–CH₃)(CH₂–CH₂–CH₃) | 92° C/0.35 mm Hg | |

[1] DNPH = 2,4-dinitrophenylhydrazone of the corresponding aldehyde

We claim:

1. 3-(4-Isopropyl-phenyl)-butanal-1.

* * * * *